United States Patent [19]

Picataggio et al.

[11] Patent Number: 5,726,053
[45] Date of Patent: Mar. 10, 1998

[54] RECOMBINANT ZYMOMONAS FOR PENTOSE FERMENTATION

[75] Inventors: Stephen K. Picataggio, Golden; Min Zhang, Lakewood, both of Colo.; Christina K. Eddy, Saratoga Springs, N.Y.; Kristine A. Deanda, Conifer, Colo.

[73] Assignee: Midwest Research Institute, Kansas City, Mo.

[21] Appl. No.: 421,996

[22] Filed: Apr. 14, 1995

Related U.S. Application Data

[63] Continuation-in-part of Ser. No. 228,303, Apr. 15, 1994, Pat. No. 5,514,583.

[51] Int. Cl.$^6$ .................... C12N 1/21; C12N 15/74; C12P 7/06
[52] U.S. Cl. .................. 435/252.3; 435/243; 435/320.1; 435/161; 435/163; 435/165; 435/822; 536/23.2; 536/23.7; 935/29; 935/60; 935/72
[58] Field of Search .................... 435/252.3, 243, 435/320.1, 161, 163, 165, 822; 536/23.2, 23.7; 935/29, 60, 72

[56] References Cited

U.S. PATENT DOCUMENTS 5,514,583  5/1996  Picataggio et al. ................. 435/252.3

OTHER PUBLICATIONS

S.D. Feldmann et al., "Pentose Metabolism in *Zymomonas mobilis* Wild–Type and Recombinant Strains", Appl. Microbiol. Biotechnol. 38: 354–361, 1992.

T. Yura et al. "Systematic Sequencing of the *Escherichia coli* Genome: Analysis of the 0–2.4 min Region", Nuc. Acids Res. (20(13): 3305–3308, Jul. 1992.

G.A. Sprenger, "Aproaches to Broaden the Substrate and Product Range of the Ethanologenic Bacterium *Zymomonas mobilis* by Genetic Engineering", J. Biotechnol. 27(3) 225–237, Feb. 1993.

N. Lee et al., "The Organization of the araBAD Operon of *Escherichia coli*", Gene 47: 231–244, 1986.

M.E. Burnett et al., "Molecular Characterization of the *Zymomonas mobilis* Enolase (eno) Gene", J. Bacteriol. 174(20): 6548–6553, Oct. 1992.

T. Conway et al., "Glyceraldehyde–3–Phosphate Dehydrogenase Gene from *Zymomonas mobilis*: Cloning, Sequencing and Identification of Promoter Region", J. Bacteriol. 169(12): 5653–5662, Dec. 1987.

C.Q. Lui et al., "Expression of Cloned Xanthomonas D–Xylose Catabolic Genes in *Zymomonas mobilis*", J. Biotechnol. 7: 61–70, 1988.

*Primary Examiner*—Rebecca E. Prouty
*Attorney, Agent, or Firm*—Edna M. O'Connor; Ken Richardson; Ruth Eure

[57] ABSTRACT

The invention relates to microorganisms which normally do not ferment pentose sugar and which are genetically altered to ferment pentose sugar to produce ethanol, and fermentation processes utilizing the same. Examples include *Zymomonas mobilis* which has been transformed with combinations of *E. coli* genes for xylose isomerase, xylulokinase, transaldolase, transketolase, L-arabinose isomerase, L-ribulokinase, and L-ribulose-5-phosphate 4-epimerase. Expression of the added genes are under the control of *Zymomonas mobilis* promoters. These newly created microorganisms are useful for fermenting pentoses and glucose, produced by hydrolysis of hemicellulose and cellulose, to produce ethanol.

12 Claims, 7 Drawing Sheets

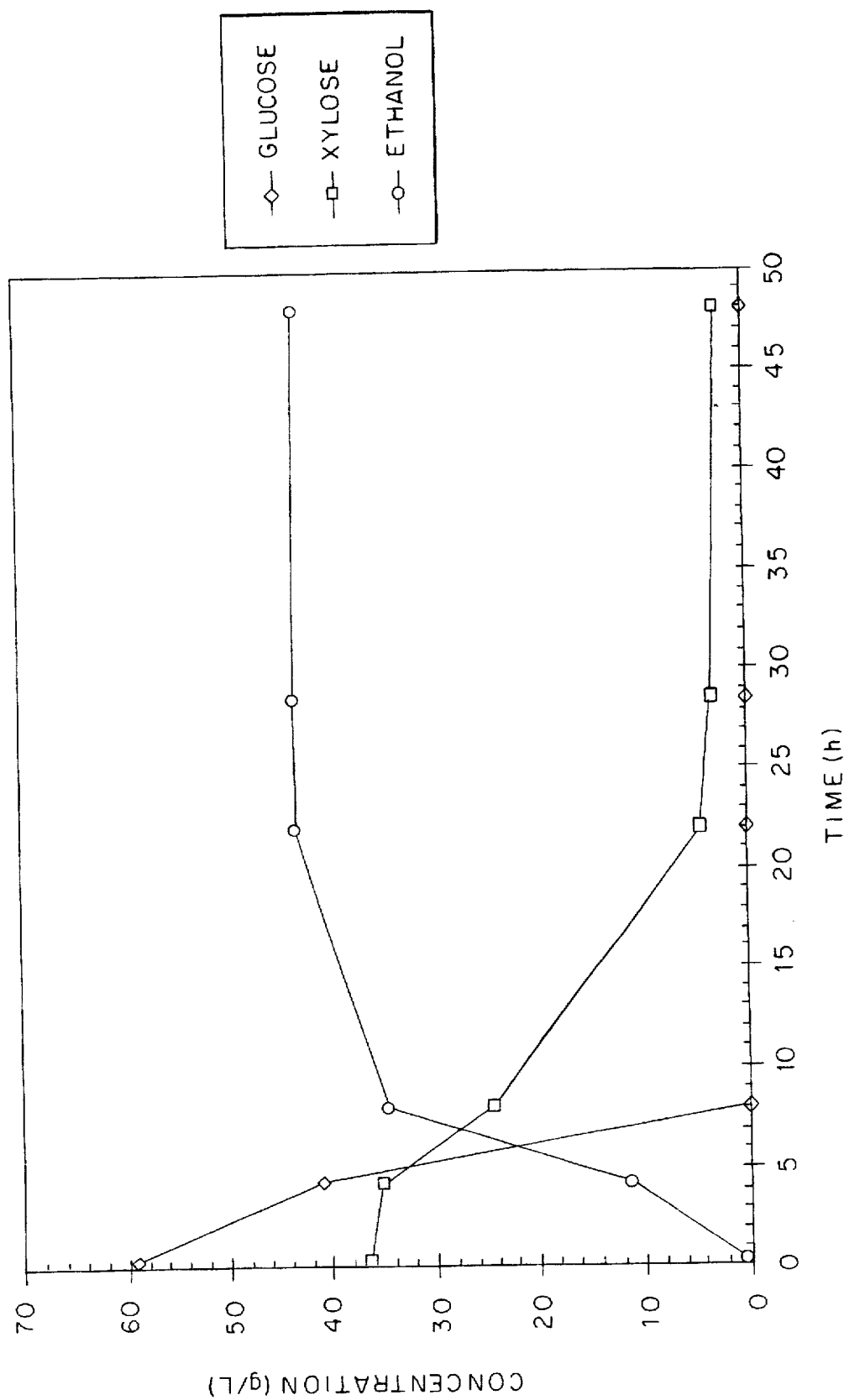

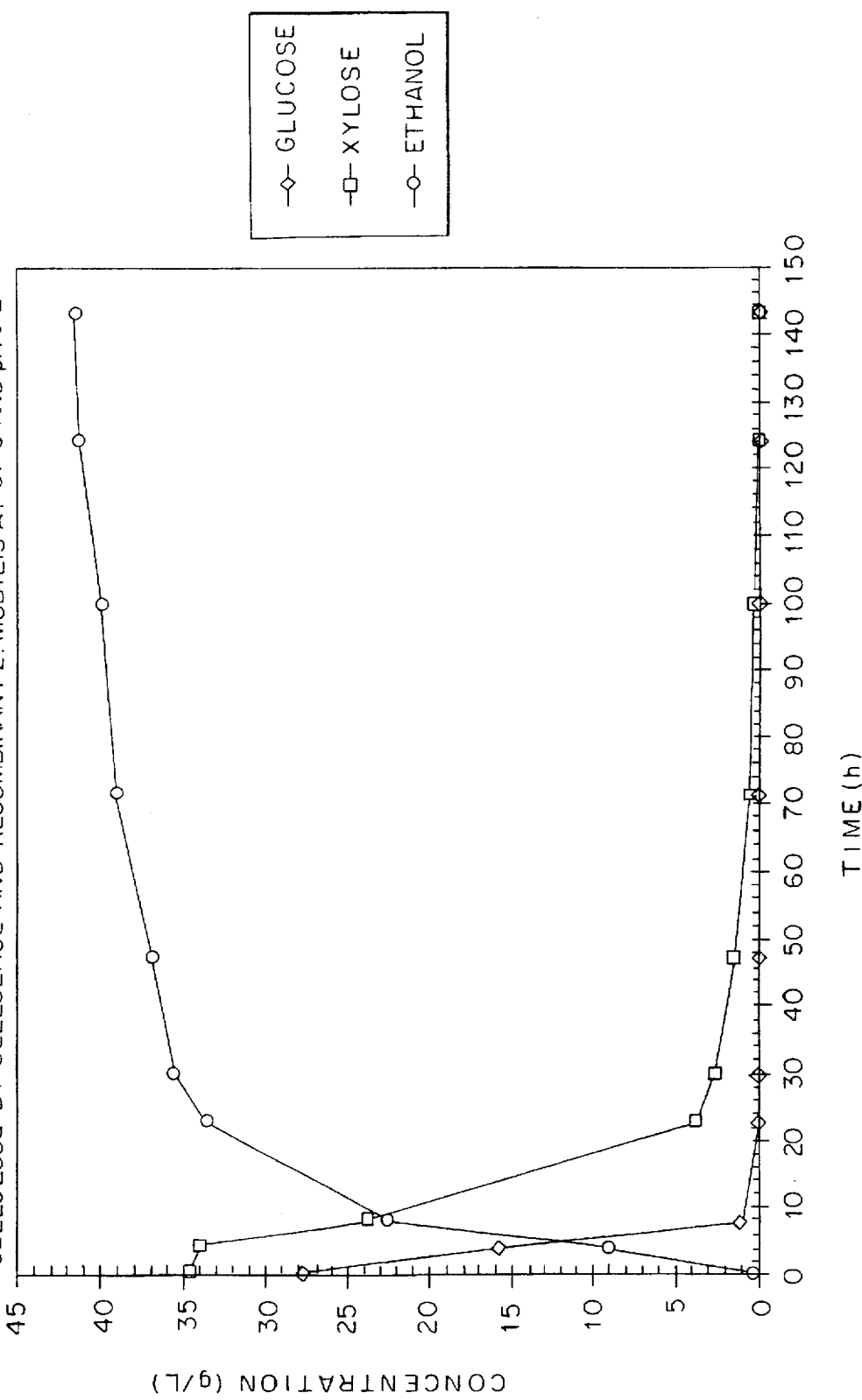

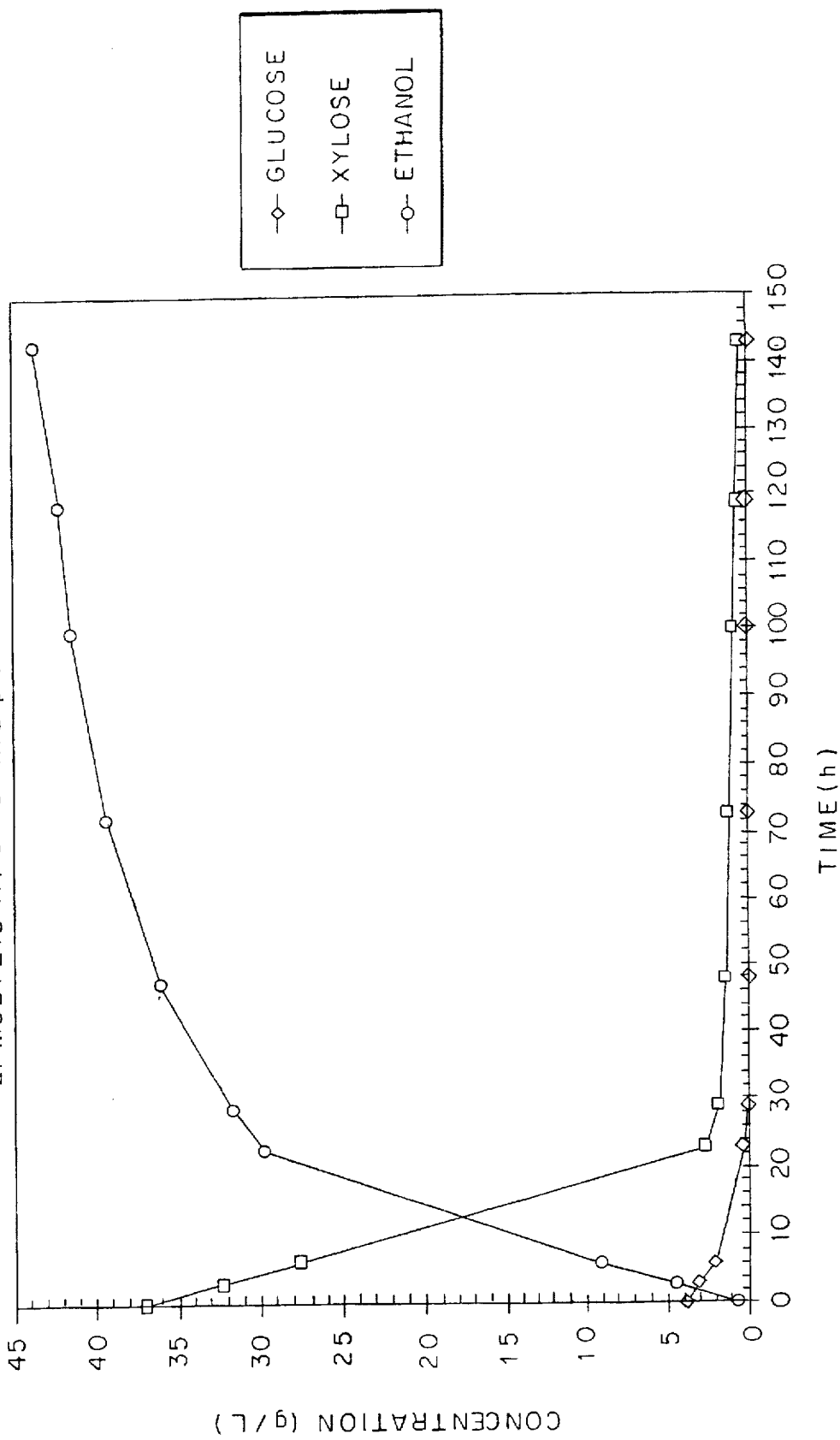

5,726,053

RECOMBINANT ZYMOMONAS FOR PENTOSE FERMENTATION

This patent application is a continuation-in-part of patent application Ser. No. 08/228,303, filed Apr. 15, 1994 now U.S. Pat. No. 5,514,583, which is incorporated herein in its entirety by reference.

CONTRACTUAL ORIGIN OF THE INVENTION

The United States Government has rights in this invention pursuant to Contract No. DE-AC36-83CH10093 between the United States Department of Energy and the Midwest Research Institute.

FIELD OF THE INVENTION

This invention relates to recombinant *Zymomonas mobilis* strains, metabolizing xylose and arabinose and bearing xylose and arabinose utilization and pentose phosphate pathway genes, useful for the fermentation of the xylose and arabinose components in cellulosic biomass to ethanol. This invention also relates to the process of using these strains for the rapid and efficient fermentation of the xylose and arabinose components in cellulosic biomass to ethanol.

BACKGROUND OF THE INVENTION

Cellulosic biomass is a favorable feedstock for fuel ethanol production because it is both readily available and less expensive than either corn or sugarcane. However, substantial hurdles must be overcome before a typical cellulosic feedstock can be utilized effectively as a substrate for the fermentative production of ethanol. The typical feedstock is comprised of approximately 35–45% cellulose, 30–40% hemicellulose, 15% lignin and 10% of other components. The cellulose fraction is comprised of polymers of the hexose sugar, glucose. The hemicellulose fraction is comprised mostly of pentose sugars, including xylose and arabinose.

Whereas microorganisms are known that can efficiently ferment the glucose component in cellulose, conversion of the xylose and arabinose in the hemicellulose fraction to ethanol has been difficult and this remains to be one of the economic bottlenecks in a biomass to ethanol conversion scheme. The rapid and efficient utilization of the xylose and arabinose components in cellulosic biomass is desirable in the development of a commercial process.

*Zymomonas mobilis* is a bacterium that has been utilized as a natural fermentative agent in the production of alcoholic beverages, such as pulque and palm wines produced from plant saps. Comparative performance trials have suggested that Zymomonas may become an important industrial ethanol-producing microorganism because of its 5–10% higher yield and up to 5-fold higher productivity compared to traditional yeast fermentations. Because of its potential value, several processes based on the use of Zymomonas for the production of industrial ethanol from glucose-based feedstocks have been disclosed in U.S. Pat. Nos. 4,731,329, 4,812,410, 4,816,399, and 4,876,196.

While Zymomonas may become an important fuel ethanol-producing microorganism from glucose-based feedstocks, its substrate utilization range is restricted to fermentation of glucose, sucrose and fructose and, is not naturally suited for fermentation of the pentose component in cellulosic feedstocks. Zymomonas contains the Entner-Douderoff pathway that allows it to ferment glucose very efficiently to ethanol as the sole fermentation product. However, Zymomonas is naturally unable to ferment the pentose sugars in cellulosic biomass because it lacks the essential pentose assimilation and metabolism pathways. Thus, an opportunity exists to genetically engineer this organism for the fermentation of pentose sugars, such as xylose and arabinose to ethanol.

Genetic engineering attempts have been made to enhance ethanol production by fermentation by transferring genes from one species to another. For example, see U.S. Pat. Nos. 5,000,000 and 5,028,539. Gene cloning and expression of various enzymes including enzymes for creating a new metabolic pathway are also known. For example see U.S. Pat. Nos. 5,272,073, 5,041,378, 5,168,056 and 5,266,475. However, none of these discoveries has successfully broadened the fermentable substrate range of a microorganism which could not previously ferment pentose sugars to ethanol.

Previous attempts to introduce a pentose catabolic pathway from either Xanthomonas or Klebsiella into Zymomonas have been unsuccessful and the recombinant strains were incapable of growth on xylose as the sole carbon source (Feldmann et al., 1992. Appl. Microbiol. Biotechnol. 38:354–361; Liu et al., 1988. J. Biotechnol. 7:61–77).

SUMMARY OF THE INVENTION

The present invention successfully introduces a catabolic pathway for fermentation of pentose sugars, such as xylose or arabinose, into a microorganism, such as Zymomonas, which previously did not have the ability to ferment pentose sugars into ethanol. For the first time, such microorganisms are capable of growing on xylose or arabinose as a sole carbon source and fermenting either of these pentoses directly to ethanol. One embodiment introduces the genes encoding xylose isomerase and xylolukinase, xylose can be converted to xylulose-5-P. Another embodiment introduces the genes encoding L-arabinose isomerase, L-ribulokinase, and L-ribulose 5-phosphate 4-epimerase, which allow the conversion of L-arabinose to D-xylulose-5-P. Then, by introducing two more genes encoding enzymes in the pentose phosphate pathway, transaldolase and transketolase, xylulose-5-P can be further converted to the key intermediates that couple pentose metabolism to the glycolytic Entner-Douderoff pathway, and consequently, permit the microorganism to metabolize pentose to ethanol. Any pentose sugar, not just arabinose and xylose, which can be converted to xylulose-5-P can be coupled to the glycolytic Enter-Douderoff pathway, and consequently to ethanol production, by the introduction of these two genes which encode transaldolase and transketolase. Accordingly, another embodiment of the present invention provides a process for fermenting any pentose sugar which can be converted to xylulose-5-P to ethanol.

One aspect of the present invention provides compositions of *Zymomonas mobilis* containing the genes encoding L-arabinose isomerase, L-ribulokinase, L-ribulose 5-phosphate 4-epimerase, transaldolase and transketolase cloned under the control of one or more *Z. mobilis* promoters such that said genes are coordinately expressed in said cells of *Z. mobilis* and confer upon said cells the ability to grow on and ferment arabinose directly to ethanol. In particular, compositions of *Z. mobilis* are provided which contain the L-arabinose isomerase, L-ribulokinase, and L-ribulose 5-phosphate 4-epimerase genes from *Escherichia coli* cloned precisely under the control of the *Z. mobilis* glyceraldehyde-3-phosphate dehydrogenase (GAP) promoter and the transaldolase and transketolase genes from

*Escherichia coli* cloned precisely under the control of the *Z. mobilis* enolase (ENO) promoter, such that all five said genes are contained on a single plasmid vector and are coordinately expressed in said cells of *Z. mobilis*, conferring upon said cells the ability to grow on and ferment arabinose directly to ethanol.

Another aspect of the present invention provides a process for producing ethanol from arabinose, or cellulosic feedstocks containing arabinose, by culturing the above mentioned genetically-engineered strains of *Z. mobilis* in a culture medium containing arabinose as a carbon source and along with an additional nitrogen source.

A further aspect of the present invention provides compositions of *Zymomonas mobilis* containing the genes encoding xylose isomerase, xylulokinase, transaldolase and transketolase which are under the control of one or more promoters recognized by *Z. mobilis*, such that these genes are expressed in *Z. mobilis*. The genes confer upon Zymomonas the ability to grow on and ferment xylose directly to ethanol upon these cells.

In particular, compositions of *Z. mobilis* are provided which contain the xylose isomerase and xylulokinase genes from *Escherichia coli* which are cloned precisely under the control of the *Z. mobilis* glyceraldehyde-3-phosphate dehydrogenase (GAP) promoter. The transaldolase and transketolase genes from *Escherichia coli* which are cloned precisely under the control of the *Z. mobilis* enolase (ENO) promoter, are also provided to *Z. mobilis*. All four of these genes are expressed in the cells of *Z. mobilis* conferring upon these cells the ability to grow on and ferment xylose directly to ethanol. The cloned genes may be provided on any number of vectors but preferably are contained on a single plasmid vector. More preferably, the genes are integrated into the host genome.

Another aspect of the present invention is cultures of microorganisms with the above described abilities. The cultures may be biologically pure, mixed together, or mixed with other strains or different organisms to aid in the metabolism of the substrates or a mixture of substrates into ethanol. A related aspect of the present invention is the culture broth per se which may tolerate a small amount of contamination.

Yet another aspect of the present invention is a process for producing ethanol from a pentose sugar, such as xylose or arabinose, mixtures thereof, or cellulosic feedstocks containing hemicellulose, by culturing the above mentioned genetically-engineered microorganisms in a culture medium containing the pentose sugars. An additional aspect of the present invention is the modification of the catabolic pathway of a microorganism, such as Zymomonas, which previously did not have the ability to ferment pentose sugars to ethanol Such microorganisms are capable of growing on arabinose or xylose as a sole carbon source and fermenting arabinose or xylose directly to ethanol. By introducing the genes for converting arabinose into ethanol, a microorganism without arabinose fermentation ability may be converted into a microorganism capable of fermenting arabinose into ethanol. Similarly, by introducing the genes for converting xylose into ethanol, a microorganism without xylose fermentation ability may be converted into a microorganism capable of fermenting xylose into ethanol.

The introduction of the genes for L-arabinose isomerase, L-ribulokinase, and L-ribulose 5-phosphate 4-epimerase in addition to transaldolase and transketolase allow a microbe, such as Zymomonas, to metabolize arabinose to ethanol. The introduction of the genes for xylose isomerase and xylolukinase, in addition to transaldolase and transketolase allow a microbe, such as Zymomonas, to metabolize xylose to ethanol.

BRIEF DESCRIPTION OF THE DRAWINGS

FIG. 5 shows the cofermentation of a mixture of xylose and glucose by the microorganism of the present invention.

FIG. 6 shows the cofermentation of a mixture of xylose, glucose and cellulose by cellulase and the microorganism of the present invention.

FIG. 7 shows the cofermentation of a mixture of xylose and cellulose by cellulase and the microorganism of the present invention.

DESCRIPTION OF THE PREFERRED EMBODIMENTS

Figure 1:
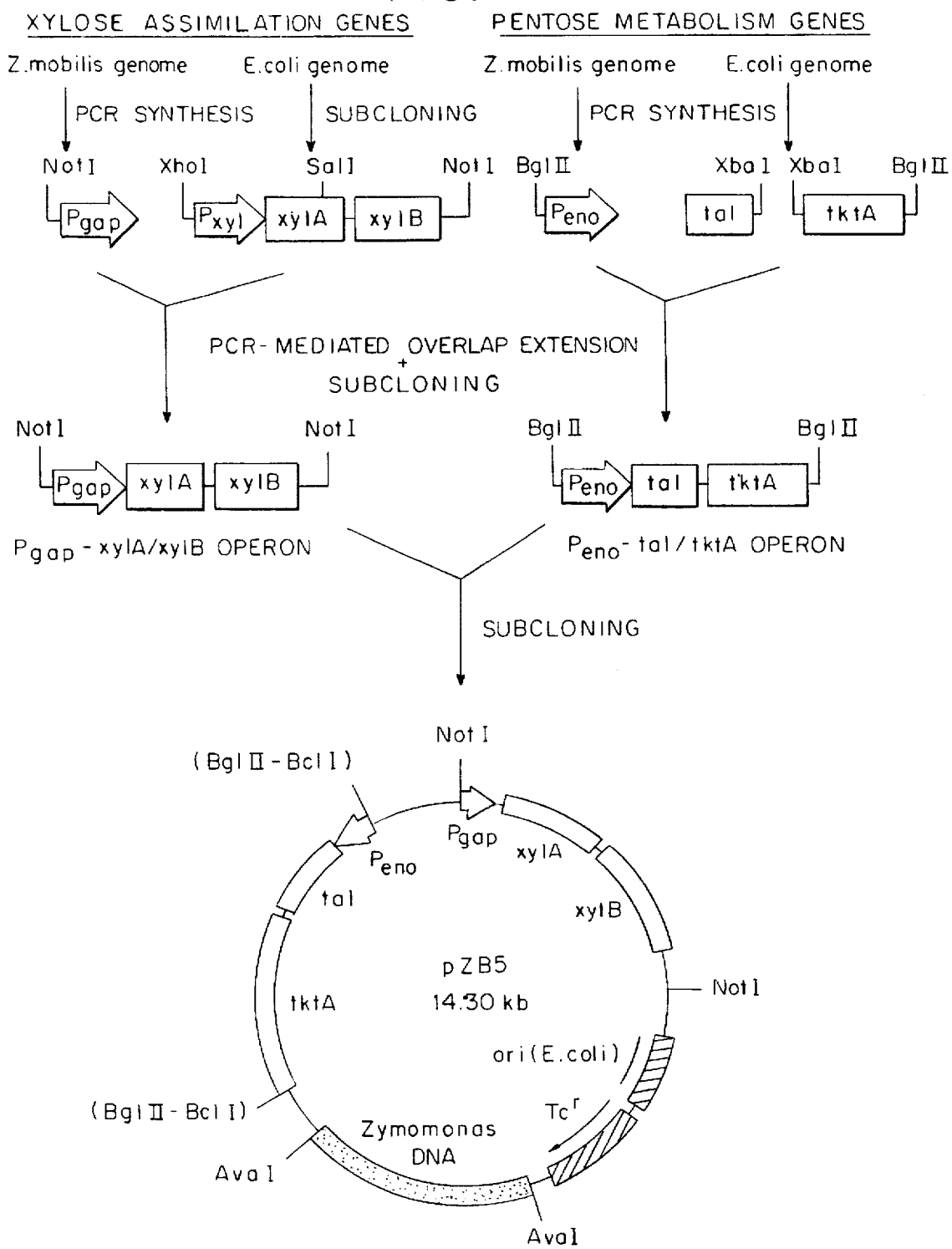
FIG. 1 shows a schematic of a process for producing the recombinant plasmid pZB5.

The invention is the development of recombinant Zymomonas and other microbial strains with an expanded substrate utilization range and which are capable of growth on and/or efficient ethanol production from xylose, arabinose or other pentose sugars, alone or in combination, as the sole carbon source.

The microorganisms used to prepare the present invention are those which are capable of being genetically altered to produce the necessary enzymes to form a metabolic pathway for catabolizing pentose sugars, particularly xylose and arabinose. The microorganism may naturally have some enzymes in the pathway but is not able to ferment xylose or arabinose into ethanol until it has been genetically altered.

The manner of genetic alteration may use any combination of known genetic engineering techniques such as mutation and addition of foreign DNA, provided that the microorganism is able to ferment a pentose sugar to ethanol after treatment. Foreign DNA may be introduced into the microorganism by any conventional technique such as conjugation, transformation, transduction or electroporation.

Many microorganisms which are capable of fermenting sugars to ethanol lack at least one of the genes for the enzymes which make up a metabolic pathway for converting xylose, arabinose and other pentose sugars into ethanol. Exogenous genes may be added to complete a metabolic pathway. One need not add genes necessary for every step if the host microorganism already produces an enzyme in the pathway. The number of genes to be added will depend on the starting microorganism. In the situation of imparting xylose fermentation capability to naturally occurring *Zymomonas mobilis*, four genes are necessary to produce enzymes to enable the pathway for metabolizing xylose to an intermediate which is further metabolized to ethanol using the glycolytic Entner-Douderoff pathway. In the situation of imparting arabinose fermentation capability to naturally occurring *Zymomonas mobilis*, five genes are necessary to produce enzymes to enable the pathway for metabolizing arabinose to an intermediate which is further metabolized to ethanol using the glycolytic Entner-Douderoff pathway.

The indigenous Zymomonas genes may be altered by any known genetic manipulation technique to provide a protein with the necessary enzyme activity to produce the desired metabolic pathway. The altered genes may complement one or more of the introduced genes from another host to complete the metabolic pathway. This procedure may be advantageous by reducing the number of genes one needs to add to the host cell. For example, Zymomonas's native transketolase may be used to substitute for a foreign transketolase gene, such as the one disclosed from *E. coli*.

Sufficient genes may be added so that the recipient microorganism may ferment xylose, arabinose or other pentose sugars as the sole carbon source. The microorganism may or may not be able to grow and multiply using xylose, arabinose, or combinations of both xylose and arabinose, as the sole carbon source, but may be capable of fermenting xylose, arabinose, or combinations of both xylose and arabinose, to ethanol.

A gene may be added to a cell by way of a vector. The vector may be in the form of a plasmid, cosmid or virus which is compatible to the celt's DNA and any resident plasmids. Generally, vectors either integrate into the recipient microorganism's DNA or the vector has an origin of replication to stably maintain the vector throughout many microbial generations. The origin of replication may code for replication under a wide range of stringency conditions.

To express the gene(s), a structural gene is generally placed downstream from a promotor region on the DNA. The promotor must be recognized by the recipient microorganism. In addition to the promotor, one may include regulatory sequences to increase or control expression. Expression may be controlled by an inducer or a repressor so that the recipient microorganism expresses the gene(s) only when desired.

In a preferred embodiment of the invention, xylose, arabinose or other pentose sugar metabolic pathway genes are obtained from pentose metabolizing microorganisms and added to Zymomonas which does not otherwise ferment pentose sugars to ethanol. Especially preferred is *Zymomonas mobilis*, which historically has been used for fermenting liquids containing sugar, such as plant sap for example, into alcoholic beverages. Certain strains of Zymomonas are tolerant of up to 1.5% sodium chloride and other mutants are tolerant to acetic acid, other microbial inhibitors, high temperatures and/or high ethanol concentrations. The selection of host strain will depend on the substrate being used.

In another embodiment of the invention, the source for the genes encoding pentose metabolism enzymes is selected from the group consisting of: Xanthomonas, Klebsiella, *E. coli*, Rhodobacter, Flavobacterium, Acetobacter, Gluconobacter, Rhizobium, Agrobacterium, Salmonella, Pseudomonads and Zymomonas. In general the source of the genes for pentose sugar metabolism is any Gram-negative bacterium capable of utilizing pentose sugars for growth. A preferred organism for the source of genes is *E. coli*. The preferred genes encode L-arabinose isomerase, L-ribulokinase, L-ribulose 5-phosphate 4-epimerase, xylose isomerase, xylulokinase, transaldolase and transketolase. Expression of these genes is under the control of promoters that function in Zymomonas. Strong glycolytic promoters are preferred. The promoters for glyceraldehyde-3-phosphate dehydrogenase and enolase are particularly preferred. Different genes may be under the control of different promoters or other expression altering sequences.

Some or all of the genes may be located together in the same vector or they may be on different vectors or integrated into the genome. Their expression may be such that the newly formed metabolic pathway is formed to enable the microorganism to ferment xylose, arabinose or other pentoses to ethanol. Preferably, the genes for L-arabinose isomerase, L-ribulokinase, L-ribulose 5-phosphate 4-epimerase, xylose isomerase, xylulokinase, transaldolase and transketolase are under the control of one or more functional promoters when in Zymomonas. The genes on a vector may be in any order, grouping or orientation relative to each other, providing that, if more than one promotor is present on the vector, the direction of transcription from one promotor does not adversely affect expression of the genes.

In other preferred embodiments of the present invention, a genetic element comprising any two or more of the above described genes may be placed on the same vector. Particularly preferred is a plasmid containing both the transaldolase and the transketolase genes. These vectors preferably have the genes under the control of a promotor recognized by Zymomonas. The Examples below show plasmids pZBET, pZB4, pZB5 and pZB206, all of which are examples of vectors carrying DNA encoding two or more of the above described genes.

The expression of the genes and the resulting functional activity of their corresponding gene products represent a new biochemical pathway that links pentose metabolism to the central Entner-Douderoff pathway in Zymomonas, conferring upon these cells, for the first time, the ability to grow on and ferment pentose directly to ethanol. The genes on a vector may be in any orientation relative to the direction of transcription of these genes provided that they do not interfere with each other. The examples below have shown that the genes perform in essentially the same way regardless of orientation.

The microorganism(s) according to the present invention may be used alone or together to ferment xylose, arabinose and other pentose sugars contained in a medium to produce ethanol. The medium may include other fermentable sugars, such as glucose. If microbial growth is desired, other nutrients necessary for microbial growth may be added and the microorganism(s) allowed to reproduce.

Transaldolase and transketolase are key enzymes of the pentose phosphate pathway and are required for fermentation by Zymomonas of any pentose sugar which can be converted to xylulose-5-P to ethanol. A preferred embodiment of the present invention is the expression of the genes for transaldolase and transketolase in Zymomonas in conjunction with any other set of genes that convert pentose sugar to xylulose-5-P. Pentose sugars suitable for fermentation by the present invention include, but are not limited to xylose and arabinose. An example of added genes needed for fermentation of arabinose are L-arabinose isomerase, L-ribulokinase, and L-ribulose 5-phosphate 4-epimerase genes in addition to transaldolase and transketolase genes. An example of added genes needed for fermentation of xylose are xylose isomerase and xylolukinase genes in addition to transaldolase and transketolase genes.

In an especially preferred embodiment of the invention, genes for xylose, arabinose and other pentose utilization, and genes for transaldolase and transketolase are obtained from organisms containing them, and are expressed in Zymomonas. Efficient transport of the pentoses into Zymomonas may be through native Zymomonas transport proteins, mutated Zymomonas transport proteins, or through the addition of new facilitated transporters introduced by cloning new transport genes into Zymomonas with or without mutagenesis of the cloned transport genes.

The step of microbial growth may be separate from fermentation. Xylose, arabinose, and other pentoses, or mixtures thereof may be used as a carbon source for microbial growth or one can separately culture the microorganisms on any medium (with or without a pentose) until sufficient numbers of microorganisms are present as a first step, and then add a medium containing a pentose for fermentation in a second step. If a two step method is used, one may control expression of the genes in the new metabolic pathway so that greater expression occurs during the second step.

The choice of substrates will depend on cost and supply of the substrate to be fermented to ethanol. A typical low-cost supply of pentoses is from hemicellulose. Xylose, arabinose and other pentoses are liberated from hemicellulosic materials by steam and/or an acid or alkali pretreatment. Smaller amounts of other sugars such as glucose are also separated during this pretreatment and are also fermented by Zymomonas to ethanol.

When the substrate is cellulosic material, the cellulose may be hydrolyzed to sugars simultaneously or separately and also fermented to ethanol. Since hemicellulose is generally easier to hydrolyze to sugars than cellulose, it is preferable to prehydrolyze the cellulosic material, separate the pentoses and then hydrolyze the cellulose by treatment with steam, acid, alkali, cellulases or combinations thereof to form glucose. Hexoses and pentoses may be fermented to ethanol simultaneously, sequentially, separately or together using the microorganisms of the present invention. If so desired, the hexoses may be fermented to ethanol by a different microorganism than the pentoses, such as yeast, natural Zymomonas, etc.

Many fermentation conditions are known per se as shown by the references mentioned in the Background of the Invention section above. *Zymomonas mobilis* is a facultative anaerobic bacterium. It has theoretical yields of ethanol from sugar of up to 97% which provides for little microbial growth, if so desired. The optimum pH conditions range from about 3.5 to about 7.5. Substrate concentrations of up to about 25% (based on glucose), and under some conditions even higher, may be used. Unlike other ethanol producing microorganisms, no oxygen is needed at any stage for microorganism survival. Also unlike yeast, oxygen does not drastically reduce ethanol production or greatly increase cell growth. Agitation is not necessary but may enhance availability of substrate and diffusion of ethanol. Accordingly, the range of fermentation conditions may be quite broad. Likewise, any of the many known types of apparata may be used for the present invention.

The microorganisms according to the present invention may be used as a biologically pure culture or may be used with other ethanol producing microorganisms in mixed culture. Microorganisms able to ferment xylose can be mixed with microorganisms able to ferment arabinose. This mixed pentose fermenting culture can be cultured itself or can then be mixed with microorganisms able to ferment glucose. Biologically pure cultures are generally easier to optimize but mixed cultures may be able to maximize substrate utilization. One may also add enzyme to the fermenter to aid in the degradation of substrates or to enhance ethanol production. For example, cellulase may be added to degrade cellulose to glucose simultaneously with the fermentation of glucose to ethanol by microorganisms in the same fermenter. Likewise, a hemicellulase may be added to degrade hemicellulose.

In the preferred embodiment using genetically engineered Zymomonas, cultures are found to be relatively resistant to contamination by other microorganisms. Nonetheless, it is preferred to eliminate or disable preexisting deleterious microorganisms in the substrate before adding the Zymomonas culture.

After fermentation, the ethanol, which may achieve concentrations of up to about 13% (w/v), is separated from the fermentation broth by any of the many conventional techniques known to separate ethanol from aqueous solutions. These methods include evaporation, distillation, solvent extraction and membrane separation. Particles of substrate or microorganisms may be removed before ethanol separation to enhance separation efficiency.

Once the fermentation is complete, excess microorganisms and unfermented substrate may be either recycled or removed in whole or in part. If removed, the microorganisms may be killed, dried or otherwise treated. This mixture may be used as animal feed, fertilizer, burnt as fuel or discarded.

While the discussion of the fermentation in this specification generally refers to a batch process, parts or all of the entire process may be performed continuously. To retain the microorganisms in the fermenter, one may separate solid particles from the fluids. This may be performed by centrifugation, flocculation, sedimentation, filtration, etc. Alternatively, the microorganisms may be immobilized before retention in the fermenter or to provide easier separation.

Unless specifically defined otherwise, all technical or scientific terms used herein have the same meaning as commonly understood by one of ordinary skill in the art to which this invention belongs. Although any methods and materials similar or equivalent to those described herein can be used in the practice or testing of the present invention, the preferred methods and materials are better illustrated by the use of the following non-limiting examples. The following examples are offered by way of illustration and not by way of limitation.

EXAMPLE 1

Isolation of the Xylose Isomerase and Xylulokinase Genes and Fusion to a Zyraoraonas GAP Promoter The *Escherichia coli* xylose isomerase and xylulokinase genes were initially obtained on a 7 kb HpaI/EcoRI restriction fragment from plasmid pLC1-3 (Clarke, L. and J. Carbon, 1977. Cell. 9:91–99). This DNA fragment was recovered from an agarose gel and subcloned into the SmaI/EcoRI sites in a pBlueScript plasmid (Stratagene, LaJolla, Calif.), which had been dephosphorylated with calf intestinal phosphatase, to generate the plasmid designated pBSX.

To remove excess DNA, pBSX was digested either with NsiI and HindHi or with NsiI and SmaI. After treatment with T4 DNA polymerase, the digested DNAs were separately ligated under dilute conditions favoring intramolecular ligation and were then transformed into *E. coli* HB 101. Restriction analyses of the plasmid DNA from ampicillin-resistant transformants confirmed the presence of the expected deletion derivatives. The plasmid with the expected 587 bp NsiI/HindIII deletion was designated pXKH and contains the xylose isomerase and xylulokinase genes with the 3'-flanking xylose operon transcriptional terminator. The plasmid with the approximately 900 bp NsiI/SmaI deletion was designated pXKS and contains the xylose isomerase and xylulokinase genes without the 3'-flanking xylose operon transcriptional terminator.

To express the xylose isomerase and xylulokinase genes in Zymomonas, they were precisely fused to a Zymomonas glyceraldehyde-3-phosphate dehydrogenase (GAP) promoter using a polymerase chain reaction (PCR)-mediated overlap extension technique. This approach allowed precise fusion of the GAP promoter containing a ribosome binding site to the translational start codon of the xylose isomerase gene, thus ensuring that the expression of the xylose isomerase and xylulokinase genes would be regulated solely by the GAP promoter.

To accomplish this precise fusion, 308 bp of 5'-flanking DNA upstream of the GAP structural gene comprising the GAP promoter and the first 893 bp of the xylose isomerase structural gene were separately synthesized in a PCR using a common linking oligonucleotide primer. The individual DNA fragments were recovered from an agarose gel and combined in a second PCR in which the complementary ends at the 3'-end of the GAP promoter and the 5'-end of the xylose isomerase gene were annealed. The addition of the 5'-GAP and 3'-xylA primers then allowed the synthesis of a 1213 bp DNA fragment comprising a precise fusion of the GAP promoter to the 5'-end of the xylose isomerase gene.

The primers used to synthesize the 308 bp DNA fragment comprising the GAP promoter were based on the known DNA sequence of the 5'-flanking region of the GAP gene (Conway et al., 1987. J. Bacteriol. 169: 5653–5662) and included:

5'-PRIMER:5'-

NotI
CCCTCGAGCGGCCGCGTTCGATCAACAACCCGAATCCTATCG-3'
(SEQ ID NO:1)

3'-PRIMER:5'-

XhoI
GGTCAAAATAGGCTTGCATGTTTATTCTCCTAACTTATTAA
GTAGCTATTATATTCC-3'(SEQ ID NO:2)

A 15 bp DNA sequence, comprising restriction sites for the restriction enzymes XhoI and NotI, was incorporated at the 5'-end of the synthesized GAP promoter. A 19 bp DNA sequence (BOLD), corresponding to the 5'-end of the xylose isomerase structural gene, was added to the 3'-end of the synthesized GAP promoter.

The primers used to synthesize the DNA fragment comprising the first 893 bp of the xylose isomerase structural gene were based on its known DNA sequence (Lawlis et al., 1984. Appl. Environ. Microbiol. 47: 15–21) and included:

5'-PRIMER:5'-
GTTAGGAGAATAAACATGCAAGCCTATTTTGACCAGCTCGATCG
CG-3'(SEQ ID NO:3)
3'-PRIMER:5'-GGTTGGCGTCGACAGAAC-3'(SEQ ID NO:4)
SalI

An 18 bp DNA sequence (BOLD), corresponding to the 3'-end of the GAP promoter was added to the 5'-end of the synthesized xylose isomerase structural gene fragment.

The 1213 bp DNA fragment, comprising a precise fusion of the GAP promoter to the 5'-end of the xylose isomerase gene was used to replace a 2.5 kb XhoI/SalI restriction fragment containing the native xylose isomerase promoter and 5'-end of the xylose isomerase gene in plasmids pXKH and pXKS. The 1213 bp DNA fragment was digested with SalI and XhoI restriction endonucleases and ligated separately to the larger of the two SalI/XhoI restriction fragments from plasmids pXKH and pXKS, previously purified by preparative agarose gel electrophoresis. The ligated DNA was used to transform E. coli HB101 and restriction analyses of the plasmid DNA from ampicillin-resistant transformants confirmed the presence of the expected plasmids, which have been designated as pGapXKH and pGapXKS. Digestion of either plasmid with the NotI restriction enzyme liberates the approximately 4.1 kb and 4.4 kb restriction fragments, respectively, containing the xylose isomerase and xylulokinase genes under the control of the GAP promoter, hereafter referred to as the GAP-xylA/xylB operon. This construct is shown in FIG. 1.

EXAMPLE 2

Isolation and Linkage of the Transaldolase and Transketolase Genes in a Synthetic Operon Under Control of a Zymomonas ENO Promoter The Escherichia coli transaldolase and transketolase genes were isolated separately, synthetically linked and precisely fused to the Zymomonas enolase (ENO) promoter by PCR-mediated overlap extension. The transaldolase gene, localized within 0'–2.5' minutes of the Escherichia coli genome, was obtained by PCR synthesis from total genomic DNA. The primers used to synthesize the 954 bp DNA fragment comprising the transaldolase gene were based on its known DNA sequence (Yura et al., 1992. Nucleic Acids Res. 20: 3305–3308) and included:

5'-PRIMER:5'-
CGTCTAAAAGATTTTAAGAAAGGTTTCGATATGACGGACAA
ATTGACC-3'(SEQ ID NO:5)
3'-PRIMER:
5'
CATTTTGACTCCAGATCTAGATTACAGCAGATCGCCGATCATTTTT
TCC-3'(SEQ ID NO:6)XbaI

A 33 bp DNA sequence (BOLD), corresponding to the 3'-end of the ENO promoter was added to the 5'-end of the synthesized transaldolase gene. A 21 bp DNA sequence comprising a restriction site for the restriction enzyme XbaI was incorporated at the 3'-end of the synthesized transaldolase gene to facilitate its subsequent subcloning.

The primers used to synthesize the 196 bp DNA fragment comprising the ENO promoter were based on the known DNA sequence of the 5'-flanking region of the ENO gene (Burnett et al., 1992. J. Bacteriol. 174: 6548–6553) and included:

5'-PRIMER:
5'-CCAGATCTCCAGTTACTCAATACG-3'(SEQ ID NO:7)
BglII
3'-PRIMER:5'-

GGTCAATTTGTCCGTCATATCGAAATTTTCTTAAAACTTTTAG
ACG-3'(SEQ ID NO:8)

A 6 bp DNA sequence comprising a restriction site for the restriction enzyme BglII was incorporated at the 5'-end of the synthesized ENO promoter to facilitate its subsequent subcloning. An 18 bp DNA sequence (BOLD), corresponding to the 5'-end of the transaldolase gene was added to the 3'-end of the synthesized ENO promoter.

The transaldolase gene (tal) was then precisely fused to the ENO promoter by PCR-mediated overlap extension. To accomplish this precise fusion, the 196 bp of 5'-flanking DNA upstream of the ENO structural gene comprising the ENO promoter and the 954 bp DNA fragment comprising the transaldolase gene were separately synthesized in a PCR using a common linking oligonucleotide primer. The individual DNA fragments were recovered from an agarose gel and then combined in a second PCR in which the complementary ends at the 3'-end of the ENO promoter and the 5'-end of the transaldolase gene were annealed. The addition of the 5'-ENO and 3'-tal primers then allowed the synthesis of a 1174 bp DNA fragment comprising a precise fusion of the ENO promoter to the transaldolase gene. This 1174 bp DNA fragment was digested with the XbaI restriction enzyme and then ligated to plasmid pUC18 that had been sequentially digested with the SmaI restriction enzyme, treated with Taq polymerase in the presence of dTTP and finally digested with XbaI. The ligated DNA was used to transform *E. coli* DH5α and restriction analyses of the plasmid DNA from ampicillin-resistant transformants confirmed the presence of the expected plasmid, which has been designated as pEnoTAL.

The transketolase gene (tktA) was obtained by PCR synthesis from *E. coli* W3110 genomic DNA. The primers used to synthesize the 2077 bp DNA fragment comprising the transketolase gene were based on its known DNA sequence (Sprenger, 1992. J. Bacteriol. 174: 1707–1708) and included:

5'-PRIMER:
5'-GCTCTAGACGATCTGGAGTCAAAATGTCC-3'(SEQ ID NO:9)
      XbaI
3'-PRIMER:
5'-AGATCTGCGCAAACGGACATTATCAAGG-3'(SEQ ID NO:10)
      BglII

A 8 bp DNA sequence comprising a restriction site for the restriction enzyme XbaI was incorporated at the 5'-end of the tktA gene and a 7 bp DNA sequence comprising a restriction site for the restriction enzyme BglII was incorporated at the 3'-end of the tktA gene to facilitate its subsequent subcloning. Following PCR synthesis, the 2077 bp DNA fragment comprising the transketolase gene was purified by preparative agarose gel electrophoresis, digested with the XbaI restriction enzyme and ligated to plasmid pUC18 that had been sequentially digested with the HincII restriction enzyme, treated with Taq polymerase in the presence of dTTP and finally digested with XbaI. The ligated DNA was used to transform *E. coli* DH5α and restriction analyses of the plasmid DNA from ampicillin-resistant transformants confirmed the presence of the expected plasmid, which has been designated as pUC-TKT.

The transketolase gene was then subcloned downstream of the ENO-transaldolase fusion to create a synthetic operon comprised of the transaldolase and transketolase genes both under the control of the ENO promoter. To do this, plasmid pUC-TKT was digested with the XbaI and SphI restriction enzymes and the approximately 2 kb restriction fragment containing the transketolase gene was purified by preparative agarose gel electrophoresis and ligated to plasmid pEno-TAL that had been previously digested with the same restriction enzymes. The ligated DNA was used to transform *E. coli* DH5α and restriction analyses of the plasmid DNA from ampicillin-resistant transformants confirmed the presence of the expected plasmid, which has been designated as pEnoTAL/TKT. Digestion of this plasmid with the BglII restriction enzyme liberates an approximately 3 kb restriction fragment containing the transaldolase and transketolase operon under the control of the ENO promoter, hereafter referred to as the ENO-tal/tktA operon. This construct is also shown in FIG. 1.

EXAMPLE 3

Construction of a Shuttle Vector and Transfer of the Xylose Metabolism and Pentose Phosphate Pathway Genes into Zymomonas A shuttle vector was constructed to permit the simultaneous transfer of the xylose metabolism and pentose phosphate pathway genes into Zymomonas. A small native 2.7 kb plasmid from *Z. mobilis* ATCC 10988 was purified by preparative agarose gel electrophoresis, linearized by digestion with the AvaI restriction enzyme and ligated to the similarly digested plasmid pACYC184 (New England BioLabs, Beverly, Mass.) which had been dephosphorylated by treatment with calf intestinal phosphatase. The ligated DNA was used to transform *E. coli* HB 101 and restriction analyses of the plasmid DNA from tetracycline-resistant transformants confirmed the presence of the expected plasmid, which has been designated as pZB186.

This plasmid was then modified to accept the xylose metabolism genes on a single NotI restriction fragment. Plasmid pZB186 was linearized with the EcoRI restriction enzyme and the cohesive ends were filled-in by treatment with the Klenow fragment of DNA polymerase. NotI linkers were added according to standard methodology and then the plasmid was digested with the NotI restriction enzyme and ligated under dilute conditions favoring intramolecular ligation. The ligated DNA was used to transform *E. coli* DH5α and restriction analyses of the plasmid DNA from tetracycline-resistant transformants confirmed the presence of the added NotI restriction site in pZB186. The modified plasmid has been designated pZB188.

To introduce the ENO-tal/tkt operon into this shuttle vector, the approximately 3 kb BglII restriction fragment from plasmid pEnoTAL/TKT was purified by preparative agarose gel electrophoresis and ligated to pZB188 that had been sequentially passaged through *E. coli* JM110, linearized by digestion with the BclI restriction enzyme and dephosphorylated by treatment with calf intestinal phosphatase. The ligated DNA was used to transform *E. coli* DH5α and restriction analyses of the plasmid DNA from tetracycline-resistant transformants confirmed the presence of the expected plasmid, which has been designated as pZBET.

To also introduce the GAP-xylA/xylB operon into this plasmid, the approximately 4.1 kb and 4.4 kb NotI restriction fragments from plasmids pGapXKH and pGapXKS, respectively, were purified by preparative agarose gel electrophoresis and separately ligated to NotI linearized pZBET. The ligated DNA was used to transform *E. coli* HB101 and restriction analyses of the plasmid DNA from tetracycline-resistant transformants confirmed the presence of the expected plasmids. The plasmid containing the GAP-xylA/xylB operon from pGapXKH in clockwise orientation and the ENO-tal/tkt operon from pEnoTAL/TKT in counterclockwise orientation has been designated pZB4. The plasmid containing the GAP-xylA/xylB operon from pGapXKS in clockwise orientation and the ENO-tal/tkt operon from pEnoTAL/TKT in counterclockwise orientation has been designated pZB5. The orientation of pZB4 and pZB5 may be viewed in FIG. 1.

Plasmids pZB4 and pZB5 were separately transformed into *Z. mobilis* CP4 by electroporation of approximately $10^9$ cells/ml with 4 µg DNA in 40 µl of 10% (w/v) glycerol at 16 kv/cm, 200 Ω and 25 µF. After electroporation, the cells were allowed to recover at 30° C. for 3–16 hours in a liquid medium comprised of 5% glucose, 10% yeast extract (Difco), 5% Tryptone (Difco), 0.25% ammonium sulfate, 0.02% potassium phosphate, dibasic and 1 mM magnesium sulfate. Transformants containing pZB4 and pZB5 were isolated following anaerobic incubation at 30° C. for 2 or more days in the same medium additionally containing 1.5% agar and tetracycline (20 µg/ml) and were subsequently confirmed by restriction analyses of the plasmid DNA from tetracycline-resistant transformants.

Enzymatic analyses of *Z. mobilis* CP4 (pZB4) demonstrated the presence of xylose isomerase (0.35 U/min/mg), xylulokinase (1.4 U/min/mg), transaldolase (1.9 U/min/mg) and transketolase (0.27 U/min/mg) activities and thus confirmed the expression of all four genes. These enzymatic activities were either undetectable or significantly lower (xylose isomerase, 0.008/min/mg; xylulokinase, undetectable; transaldolase, 0.014 U/min/mg; and transketolase, 0.032 U/min/mg) in the control strain containing the shuttle vector alone (CP4 [pZB 186]).

EXAMPLE 4

Fermentation Performance of Recombinant Zymomonas Containing the Xylose Metabolism and Pentose Phosphate Pathway Genes The fermentation performance of the recombinant Zymomonas containing the xylose isomerase, xylulokinase, transaldolase and transketolase genes was evaluated in a medium comprising 1% (w/v) yeast extract (Difco), 0.2% potassium phosphate, dibasic and either 5% glucose, or 5% xylose, or 2.5% glucose and 2.5% xylose.

The recombinant Zymomonas strains were first propagated at 30° C. in the above medium containing 5% glucose or xylose in a bottle with 80 ml of working volume without agitation until late log-phase. The cells were then inoculated to 200 ml of the above fermentation medium in a 250 ml flask at an initial $OD_{600}$=0.05–0.1. The cultures were grown at 30° C. under anaerobic conditions using $CO_2$-traps with gentle shaking (150 rpm) for mixing. The cell growth was monitored as optical density at 600 nm. The residual sugars as well as ethanol concentrations were determined on HPLC (HP 1090L) (Hewlett Packard, Wilmington, Del.) using a Bio-Rad Aminex HPX-97H column.

Figure 2:
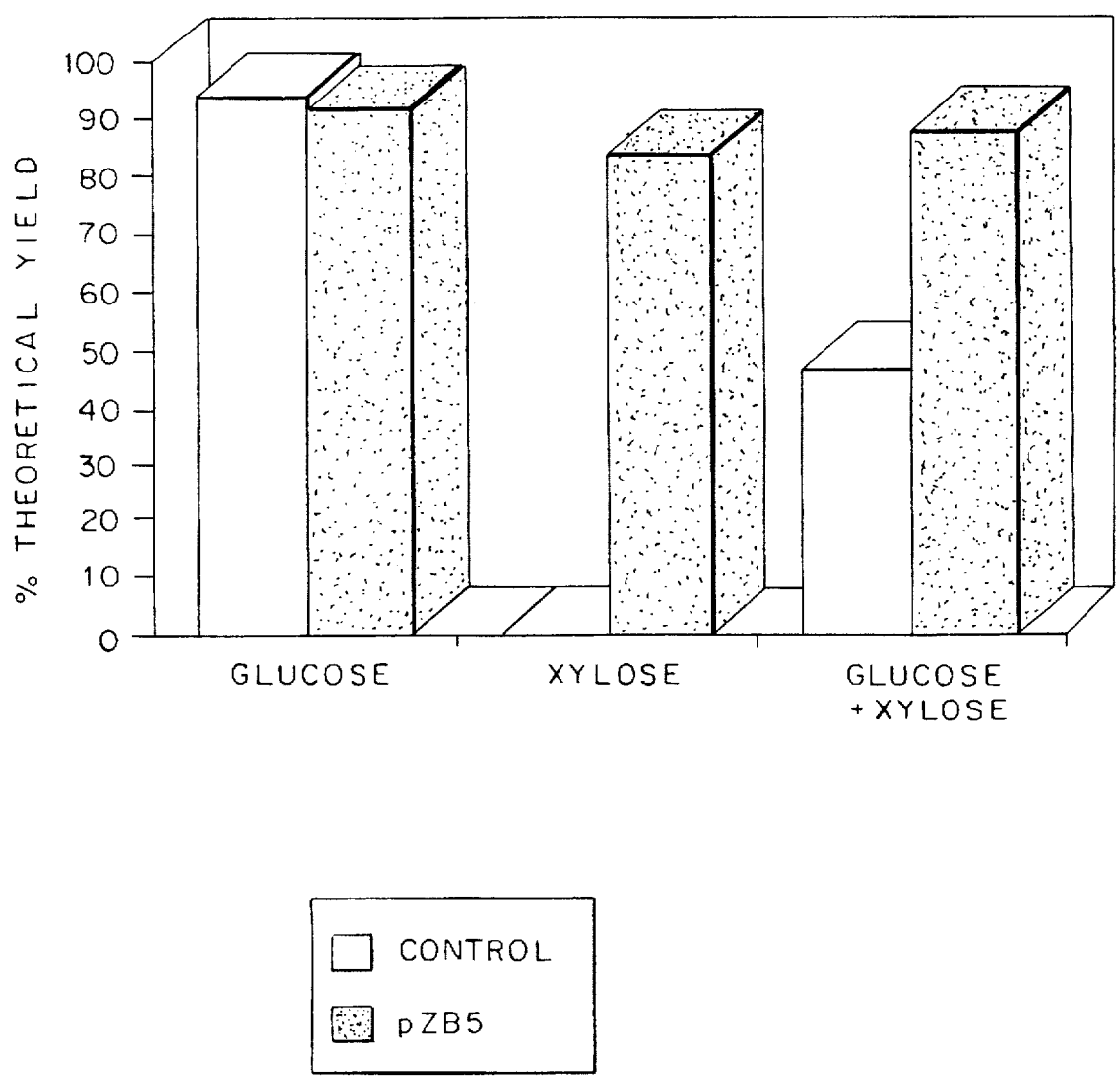
FIG. 2 shows the comparative yield of ethanol using a control *Zymomonas mobilis* and the present recombinant strain containing pZB5 when grown on glucose, xylose or a mixture of the two sugars of sugars as the carbon source.

The results presented in FIG. 2 show that in contrast to the control strain containing the shuttle vector alone (CP4[pZB 186]), the recombinant containing the added xylose isomerase, xylulokinase, transaldolase and transketolase genes demonstrated growth and ethanol production from xylose as a carbon source. The recombinant strain produces ethanol from glucose as efficiently as the control strain at 94% of theoretical yield. The recombinant strain additionally produces ethanol from xylose at 84% of theoretical yield in 79 hours. Furthermore, in the combined presence of glucose and xylose, the recombinant strain ferments both sugars simultaneously to ethanol at 88% of theoretical yield within 48 hours, thus providing the foundation for advanced process designs with cofermentation of mixed-sugar feedstocks.

EXAMPLE 5

Isolation of the L-Arabinose Isomerase, L-Ribulokinase, and L-Ribulose 5-Phosphate 4-Epimerase Genes and Fusion to a Zymomonas GAP Promoter The L-arabinose isomerase (araA), L-ribulokinase (araB), and L-ribulose 5-phosphate 4-epimerase (araD) genes were isolated separately from the native araBAD operon of *Escherichia coli* B/r (Lee et al., 1986, Gene 47:231–244) using polymerase chain reaction (PCR) synthesis, and synthetically linked to form a new araBAD operon. To express the L-ribulokinase, L-arabinose isomerase, and L-ribulose 5-phosphate 4-epimerase (araBAD) genes in Zymomonas, the genes were precisely fused to a Zymomonas glyceraldehyde-3-phosphate dehydrogenase (GAP) promoter using a PCR-mediated overlap extension technique. This approach allowed precise fusion of the GAP promoter containing a ribosome binding site to the translational start codon of the L-ribulokinase gene, thus ensuring that the expression of the araBAD genes would be regulated solely by the GAP promoter. To accomplish this precise fusion, 308 bp of 5'-flanking DNA upstream of the GAP structural gene comprising the GAP promoter and the first 582 bp of the araB structural gene were separately synthesized in a PCR using a common linking oligonucleotide primer. The individual DNA fragments were recovered from an agarose gel and combined in a second PCR in which the complementary ends at the 3'-end of the GAP promoter and the 5'-end of the araB gene were annealed. The addition of the 5'-GAP and 3'-araB primers then allowed the synthesis of a 902 bp DNA fragment comprising a precise fusion of the GAP promoter to arab gene.

The primers used to synthesize the 308 bp DNA fragment comprising the GAP promoter were based on the known DNA sequence of the 5'-flanking region of the GAP gene (Conway et al., 1987, J. Bacteriol. 169: 5653–5662) and included:

5'-PRIMER:
NotI
5'-GGAATTCGCGGCCGCGTTCGATCAACAACCCGAATCC-3'
EcoRI
(SEQ ID NO:11)
3'-PRIMER:
5'-CAATTGCAATCGCCATGTTTATTCTCCTAACTTATTAA
GTAGCTATTATATTCC-3'(SEQ ID NO:12)

A 15 bp DNA sequence, comprising restriction sites for the restriction enzymes EcoRI and NotI, was incorporated at the 5'-end of the synthesized GAP promoter. A 16 bp DNA sequence (BOLD), corresponding to the 5'-end of araB gene, was added to the 3'-end of the synthesized GAP promoter.

The primers used to synthesize the DNA fragment comprising the first 582 bp of the araB gene were based on its known DNA sequence (Lee et al., 1986, Gene 47: 231–244) and included:

5'-PRIMER:5'-
GTTAGGAGAAACATGGCGATTGCAATTGGCCTCGATTTTGGC-3'
(SEQ ID NO:13)
3'-PRIMER:
5'-CGGGCGGGTGGTACCGGAAAG-3'(SEQ ID NO:14)
KpnI

A 15 bp DNA sequence (BOLD), corresponding to the 3'-end of the GAP promoter was added to the 5'-end of the synthesized araB gene fragment.

Following the second PCR synthesis, the 902 bp PCR fragment was purified by preparative agarose gel electrophoresis and digested with EcoRi and KpnI to generate the 891 bp EcoRI-KpnI DNA fragment, comprising a precise fusion of the GAP promoter to the arab gene.

The 2679 bp DNA fragment, comprising the 3'-end of the araB and araA genes was obtained by PCR synthesis from the *Escherichia coli* B/r chromosome. The primers used to synthesize this DNA fragment were based on its known DNA sequence (Lee et al., 1986, Gene 47: 231–244) and included:

5'-PRIMER:5'-CTTTCCGGTACCACCCGCCCG-3'(SEQ ID NO:15)
        KpnI
3'-PRIMER:
5'-CTAACATGTTGACTCCTTCTCTAGACTTAGCGACGAAATCCGTAATACAC-3'
                      XbaI
(SEQ ID NO:16)

A 26 bp DNA sequence, comprising restriction site for XbaI, was incorporated at the 3'-end of the araA gene. Following PCR synthesis, the 2679 bp PCR fragment was purified by preparative agarose gel electrophoresis, digested with KpnI and XbaI to generate the 2652 bp KpnI-XbaI DNA fragment, comprising the 3'-end of the araB and the araA genes.

Figure 3:
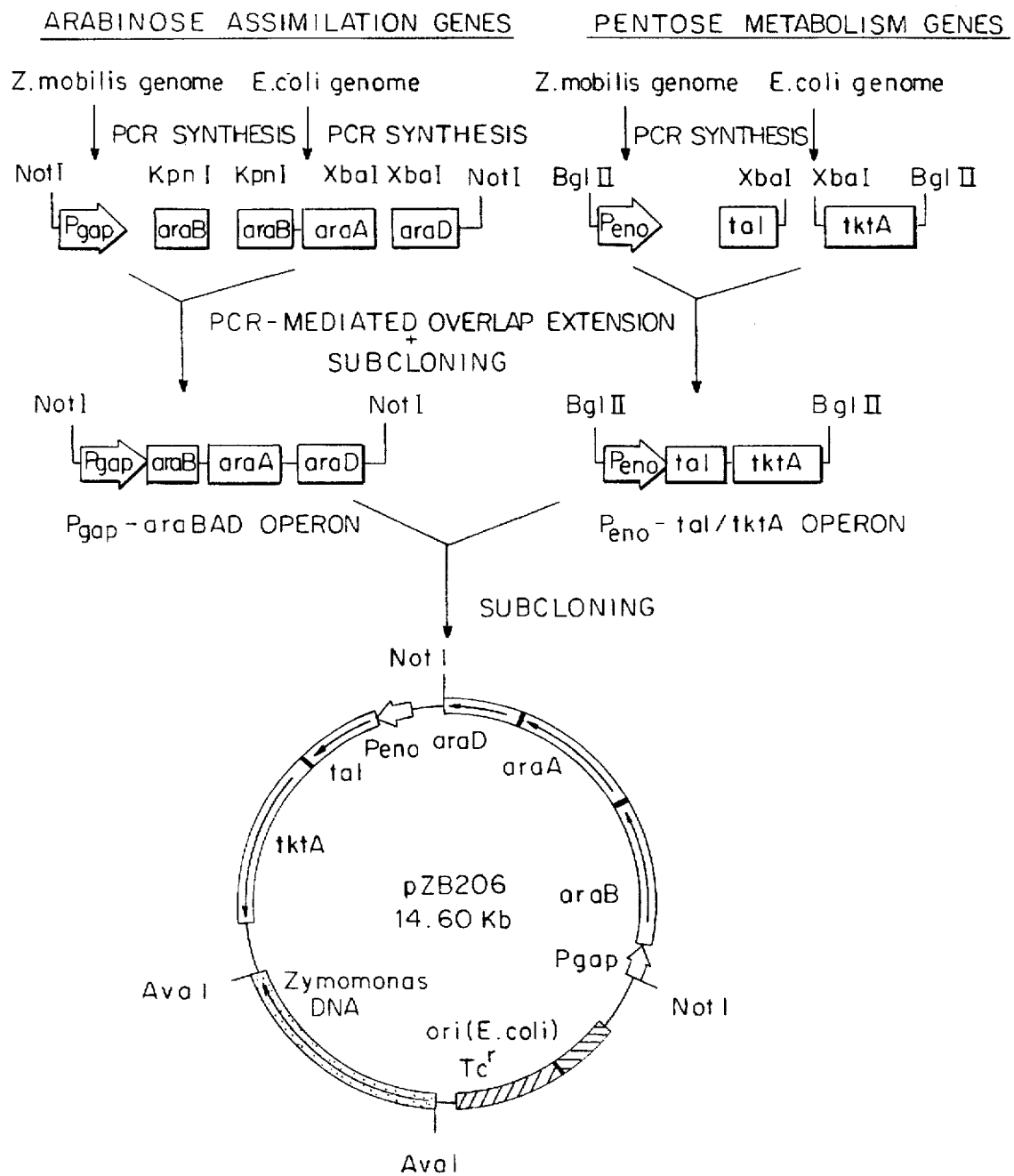
FIG. 3 shows a schematic of a process for producing the recombinant plasmid, pZB206.

To remove the repetitive extragenic palindromic sequences between araA and araD in the native araBAD operon, the araD gene encoding L-ribulose 5-phosphate 4-epimerase was isolated separately from the *Escherichia coli* B/r chromosome using PCR synthesis, then linked to 3'-end of araA to form a new araBAD operon. The primers used to synthesize the 916 bp DNA fragment comprising the araD gene were based on its known DNA sequence (Lee et al., 1986, Gene 47:231–244) and included:

DNA fragment, comprising a precise fusion of the GAP promoter to the arab gene, was then ligated to pBRMCS-araB'AD that had been digested with KpnI and EcoRI restriction enzymes. The ligated DNA was used to transform *E. coli* DH5a and restriction analyses of the plasmid DNA from ampicillin-resistant transformants confirmed the presence of the expected plasmid, which has been designated as pBR gap-araBAD. Digestion of this plasmid with the NotI restriction enzyme liberates an approximately 4.4 kb restriction fragment containing the L-arabinose isomerase, L-ribulokinase, and L-ribulose 5-phosphate 4-epimerase operon under the control of the GAP promoter, hereafter referred to as the $P_{gap}$-araBAD operon (FIG. 3).

5'-PRIMER:5'-
CGGATTTCGTCGCTAAGTCTAGAGAAGGAGTCAACATGTTAGAAGATCTC-3'(SEQ ID NO:17)
                 XbaI
3'-PRIMER:5'-
CCCCCAAGCTTGCGGCCGCGGCCCGTTGTCCGTCGCCAG-3'(SEQ ID NO:18)
     HindIII    NotI A 23 bp DNA sequence, comprising a restriction site for XbaI, was incorporated at the 5'-end of the araD gene and a 19 bp DNA sequence, comprising restriction sites for HindIII and NotI, was incorporated at the 3'-end of the araD gene to facilitate its subsequent subcloning. Following PCR synthesis, the 916 bp PCR fragment was purified by preparative agarose gel electrophoresis and digested with the XbaI and HindIII to generate the 892 bp DNA fragment, comprising the araD gene, that was ligated to plasmid pUC18 that had been digested with the same restriction enzymes. The ligated DNA was used to transform *E. coli* DH5a and restriction analyses of the plasmid DNA from ampicillin-resistant transformants confirmed the presence of the expected plasmid, which has been designated as pUC-araD.

To construct a new araBAD operon, araD was linked to the 3'-end of the araA. To do this, the 2652 bp KpnI-XbaI DNA fragment, comprising the 3'-end of the araB and the araA genes was ligated to pUC-araD that had been digested with KpnI and XbaI restriction enzymes. The ligated DNA was used to transform *E. coli* DH5a and restriction analyses of the plasmid DNA from ampicillin-resistant transformants confirmed the presence of the expected plasmid, which has been designated as pUC-araB'AD. The plasmid pUC-araB'AD contains the partial new araBAD operon.

The plasmid pBRMCS which was constructed by inserting the EcoRI-HindIII multiple cloning site fragment of pUC18 into the EcoRI and HindIII sites in pBR322, was used to subclone the new $P_{gap}$-araBAD operon (see below). The 3544 bp ara-B'AD fragment was isolated by preparative agarose gel electrophoresis following digestion of pUC-araB'AD with KpnI and HindIII, and ligated to pBRMCS that had been digested with the same restriction enzymes. The ligated DNA was used to transform *E. coli* DH5a and restriction analyses of the plasmid DNA from ampicillin-resistant transformants confirmed the presence of the expected plasmid, which has been designated as pBRMCS-AraB'AD. The previously obtained 891 bp EcoRI-KpnI

EXAMPLE 6

Construction of a Recombinant Plasmid Containing Arabinose Metabolism and Pentose Phosphate Pathway Genes and Transfer into Zymomonas The plasmids pZBET containing the $P_{eno}$-tal/tkt A operon comprising the transaldolase and transketolase genes from *Escherichia coli* cloned precisely under the control of the *Z. mobilis* enolase (ENO) promoter in both clockwise and counterclockwise orientations were previously constructed in Example 2. To introduce the $P_{gap}$-araBAD operon into this plasmid, the approximately 4.4 kb NotI restriction fragment from plasmids pBR gap-araBAD was purified by preparative agarose gel electrophoresis and separately ligated to NotI linearized pZBET. The ligated DNA was used to transform *E. coli* DH5a and restriction analyses of the plasmid DNA from tetracycline-resistant transformants confirmed the presence of the expected plasmids. The plasmid containing the Peno-tal/tkt A operon and the $P_{gap}$-araBAD operon in clockwise orientations has been designated pZB200. The plasmid containing the $P_{eno}$-tal/tkt A operon in clockwise orientation and the $P_{gap}$-araBAD operon in counterclockwise orientation has been designated pZB202. The plasmid containing the $P_{eno}$-tal/tkt A operon in counterclockwise orientation and the Pg$_{gap}$-araBAD operon in clockwise orientation has been designated pZB204. The plasmid containing the $P_{eno}$-tal/tkt A operon and the $P_{gap}$-araBAD operon in counterclockwise orientations has been designated pZB206 (FIG. 3).

Plasmids pZB200, pZB202, pZB204 and pZB206 were separately transformed into *Z. mobilis* ATCC 39676 by electroporation of approximately $10^9$ cells/ml with 1.2 to 3.0 μg DNA in 40 μl of 10% (w/v) glycerol at 16 kv/cm, 200 Ω and 25 μF. After electroporation, the cells were allowed to recover at 30° C. for 3–16 hours in a liquid medium comprised of 5% glucose, 10% yeast extract (Difco), 5% Tryptone (Difco), 0.25% ammonium sulfate, 0.02% potassium phosphate, dibasic and 1 mM magnesium sulfate.

Transformants containing pZB200, pZB202, pZB204 and pZB206 were isolated following anaerobic incubation at 30° C. for 2 or more days in the same medium additionally containing 1.5% agar and tetracycline (20 µml) and were subsequently consumed by restriction analyses of the plasmid DNA from tetracycline-resistant transformants.

EXAMPLE 7

Fermentation Performance of Recombinant Zymomonas Containing the Arabinose Metabolism and Pentose Phosphate Pathway Genes The fermentation performance of the recombinant Zymomonas containing the L-arabinose isomerase, L-ribulokinase, L-ribulose 5-phosphate 4-epimerase, transaldolase and transketolase genes was evaluated in a medium comprised of 1% (w/v) yeast extract (Difco), 0.2% potassium phosphate, dibasic and either 2.5% arabinose or 2.5% arabinose and 2.5% glucose. The recombinant Zymomonas strains were first propagated at 30°C. in above medium containing 5% glucose till late logphase. The cells were then inoculated to 95 ml of fermentation medium in a 100 ml bottle at an initial $OD_{600}$=0.15 at 600 nm. The culture was grown at 30°C. or 37°C. without shaking.

Figure 4:
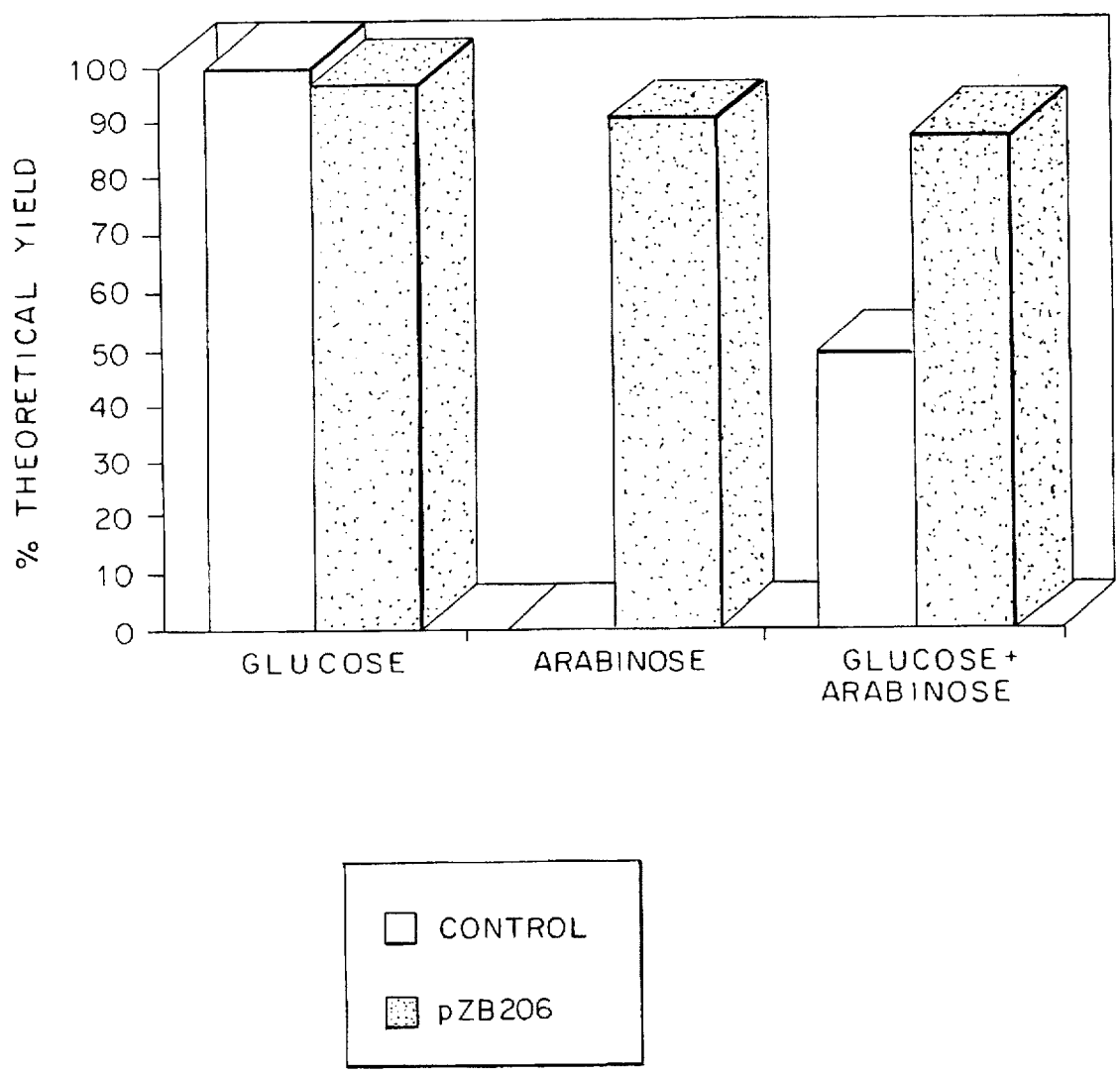
FIG. 4 shows the comparative yield of ethanol using a control *Zymomonas mobilis* and the present recombinant strain containing pZB206 when grown on glucose, arabinose or a mixture of the two sugars as the carbon source.

The results presented in FIG. 4 show that, in contrast to the control strain containing the shuttle vector alone (pZB186), the recombinant strain containing the added L-arabinose isomerase, L-ribulokinase, L-ribulose 5-phosphate 4-epimerase, transaldolase and transketolase genes (pZB206) demonstrates growth on and ethanol production from arabinose as a sole carbon source. The recombinant strain of the present invention produces ethanol from arabinose at 91% or 96% of theoretical consumed sugar yield in 96 hours at 30° C. or 37° C., respectively. Furthermore, in the combined presence of glucose and arabinose, the recombinant strain ferments both sugars to ethanol at 89% or 96% of theoretical consumed sugar yield in 96 hours at 30° C. or 37° C., respectively, thus providing the foundation for advanced process designs requiring cofermentation of mixed-sugar feedstocks.

EXAMPLE 8

Using Recombinant Zymomonas Containing the Xylose Metabolism and Pentose Phosphate Pathway Genes to Coferment Glucose and Xylose The fermentation performance of the recombinant Zymomonas containing the D-xylose isomerase, D-xylulokinase, transaldolase, and transketolase genes was evaluated on a mixture of 3.5% (w/v) D-xylose and 6% (w/v) D-glucose. Fermentation was carried out in an unsparged 500 mL working volume fermenter operating at a temperature of 37° C., an agitation rate of 150 rpm, and was inoculated with approximately 0.6 g of dry cell mass per liter (g DCM/L). The fermentation pH was controlled at 5.2 by the automatic addition of concentrated potassium hydroxide. The fermentation medium comprised 1% (w/v) yeast extract (Difco) and 0.2% (w/v) dibasic potassium phosphate; tetracycline was added at a level of 10 mg/L to ensure plasmid retention.

The recombinant strain from Example 3 containing the added genes encoding enzymes for xylose utilization fermented the mixture of 6% (w/v) glucose and 3.5% (w/v) xylose to about 42 g/L ethanol in 48 hours to achieve an overall (net) yield of available sugars of 86% of theoretical. See FIG. 5.

EXAMPLE 9

Using Recombinant Zymomonas Containing the Xylose Metabolism and Pentose Phosphate Pathway Genes to Coferment Cellulose, Glucose and Xylose The fermentation performance of the recombinant Zymomonas containing the D-xylose isomerase, D-xylulokinase, transaldolase, and transketolase genes as produced in Example 3 was evaluated on a mixture of 3.5% (w/v) D-xylose, 3% (w/v) D-glucose and 3% (w/v) Sigmacell-50 microcrystalline cellulose (Sigma). CPN cellulase enzyme complex (Iogen) was added at a loading of 25 filter paper units per gram of cellulose (FPU/g cellulose) to hydrolyze the cellulose. Fermentation was carried out in an unsparged 500 mL working volume fermenter at a temperature of 37° C. and an agitation rate of 150 rpm, and was inoculated with approximately 0.6 g of dry cell mass per liter (g DCML). The fermentation pH was controlled at 5.2 by the automatic addition of concentrated potassium hydroxide. The fermentation medium comprised 1% (w/v) yeast extract (Difco) and 0.2% (w/v) dibasic potassium phosphate; tetracycline was added at a level of 10 mg/L to ensure plasmid retention.

In the presence of exogenous cellulase, the recombinant strain produced by Example 3 above, containing the added genes encoding for xylose utilization fermented the mixture of 3% (w/v) cellulose, 3% (w/v) glucose and 3.5% (w/v) xylose to about 40 g/L ethanol in 120 hours to achieve an overall (net) yield on all potentially available sugars above 80% of theoretical. See FIG. 6.

EXAMPLE 10

Using Recombinant Zymomonas Containing the Xylose Metabolism and Pentose Phosphate Pathway Genes to Coferment Cellulose and Xylose The fermentation performance of the recombinant Zymomonas containing the D-xylose isomerase, D-xylulokinase, transaldolase, and transketolase genes was evaluated on a mixture of 3.5% (w/v) D-xylose and 6% (w/v) Sigmacell-50 microcrystalline cellulose (Sigma). CPN cellulase enzyme complex (Iogen) was added at a loading of 25 filter paper units per gram of cellulose (FPU/g cellulose) to hydrolyze the cellulose. Fermentation was carried out in an unsparged 500 mL working volume fermenter operating at a temperature of 37° C. and an agitation rate of 150 rpm, and was inoculated with approximately 0.6 g of dry cell mass per liter (g DCM/L). The fermentation pH was controlled at 5.2 by the automatic addition of concentrated potassium hydroxide. The fermentation medium comprised 1% (w/v) yeast extract (Difco) and 0.2% (w/v) dibasic potassium phosphate; tetracycline was added at a level of 10 mg/L to ensure plasmid retention.

As shown in FIG. 7, in the presence of exogenous cellulase, the recombinant strain produced by Example 3 above, containing the added genes encoding for xylose utilization fermented the mixture of 6% (w/v) cellulose and 3.5% (w/v) xylose to about 38 g/L ethanol in 120 hours to achieve an overall (net) yield on all potentially available sugars above 72% of theoretical.

EXAMPLE 11

Using Recombinant Zymomonas Containing the Arabinose Metabolism and Pentose Phosphate Pathway Genes to Coferment Cellulose, Glucose and Arabinose Fermentation of mixtures of L-arabinose, D-glucose, and cellulose can be carried out using the recombinant Zymomonas containing the L-arabinose isomerase, L-ribulokinase, L-ribulose 5-phosphate 4-epimerase, transaldolase, and transketolase genes in a manner similar to that described in Example 7 above. Using this approach, yields based on total potentially available sugars (D-glucose+L-arabinose) of greater than 75% could be achieved. For example, mixtures of 2.5% (w/v) L-arabinose, 2.5% (w/v) D-glucose, and 2.5% (w/v) Sigmacell-50 microcrystalline cellulose (Sigma) could be fermented in an unsparged 500 mL working volume fermenter operating at a temperature of 37° C., an agitation rate of 150 rpm, using an inoculum loading of approximately 0.6 g of dry cell mass per liter (g DCM/L). In this case, a cellulase enzyme complex such as CPN cellulase (Iogen) would be added at an appropriate loading, such as 25 filter paper units per gram of cellulose (FPU/g cellulose), to hydrolyze the cellulose. Fermentation pH would be controlled at an appropriate level to uncouple fermentation from growth, such as pH 5.2 by the automatic addition of concentrated potassium hydroxide. The fermentation medium would be comprised of 1% (w/V) yeast extract (Difco) and 0.2% (w/v) dibasic potassium phosphate, and tetracycline added at a level of approximately 10 mg/L to ensure plasmid retention.

EXAMPLE 12

Using Recombinant Zymomonas Containing the Arabinose Metabolism and Pentose Phosphate Pathway Genes to Coferment Cellulose and Arabinose Fermentation of mixtures of L-arabinose and cellulose can be carried out using the recombinant Zymomonas containing the L-arabinose isomerase, L-ribulokinase, L-ribulose 5-phosphate 4-epimerase, transaldolase, and transketolase genes in a manner similar to that described in Example 10 above. Using this approach, yields based on total potentially available sugars (D-glucose+L-arabinose) of greater than 70% could be achieved. For example, mixtures of 2.5% (w/v) L-arabinose and 5% (w/v) Sigmacell-50 microcrystalline cellulose (Sigma) could be fermented in an unsparged 500 mL working volume fermenter operating at a temperature of 37° C., an agitation rate of 150 rpm, using an inoculum loading of approximately 0.6 g of dry cell mass per liter (g DCM/L). In this case, a cellulase enzyme complex such as CPN cellulase (Iogen) would be added at an appropriate loading, such as 25 filter paper units per gram of cellulose (FPU/g cellulose), to hydrolyze the cellulose. Fermentation pH would be controlled at an appropriate level such as pH 5.2 by the automatic addition of concentrated potassium hydroxide. The fermentation medium would be comprised of 1% (w/v) yeast extract (Difco) and 2% (w/v) dibasic potassium phosphate, and tetracycline added at a level of approximately 10 mg/L to ensure plasmid retention.

EXAMPLE 13

Using Mixed Cultures of the Recombinant Zymomonas Containing the Xylose Metabolism and Pentose Phosphate Pathway Genes in Combination with the Recombinant Zymomonas Containing the Arabinose Metabolism and Pentose Phosphate Pathway Genes to Coferment Mixtures of Xylose and Arabinose and Glucose, Mixtures of Xylose and Arabinose and Cellulose, or Mixtures of Xylose and Arabinose and Glucose and Cellulose Fermentation of mixtures of L-arabinose, D-xylose, D-glucose, and cellulose can be carried out by using a mixed cultured comprised of the recombinant Zymomonas containing the L-arabinose isomerase, L-ribulokinase, L-ribulose 5-phosphate 4-epirnerase, transaldolase, and transketolase genes in combination with the recombinant Zymomonas containing the D-xylose isomerase, D-xylulokinase, transaldolase, and transketolase genes. Using this approach, yields based on total potentially available sugars (D-glucose+D-xylose+L-arabinose) of greater than 70% could be achieved. For example, mixtures of 2% (w/v) L-arabinose, 2% (w/v) D-xylose, 2% (w/v) D-glucose, and 2% (w/v) Sigmacell-50 microcrystalline cellulose (Sigma) could be fermented in an unsparged 500 mL working volume fermenter operating at a temperature of 37° C., an agitation rate of 150 rpm, using an inoculum loading of approximately 0.3 g of dry cell mass per liter (g DCM/L) of the arabinose-fermenting strain in combination with approximately 0.3 g of dry cell mass per liter (g DCM/L) of the xylose-fermenting strain. Inoculum ratios of the two recombinant strains can be varied from 1:1, as recited herein, to equal the proportion of the arabinose:xylose ratio in the mixture. In this particular example, since cellulose is present, a cellulase enzyme complex such as 25 filter paper units per gram of cellulose (FPU/g) is added to hydrolyze the cellulose. If a mixture of only L-arabinose, D-xylose, and D-glucose were to be fermented, it would not be necessary to add cellulase enzyme complex. Fermentation pH would be controlled at an appropriate level such as pH 5.2 by the automatic addition of concentrated potassium hydroxide. The fermentation medium would be comprised of 1% (w/v) yeast extract (Difco) and 0.2% (w/v) dibasic potassium phosphate, and tetracycline added at a level of approximately 10 mg/L to ensure retention of the plasmids by both of the strains. Since growth would be minimized by operating at 37 ° C., one of the strains would not outcompete or overtake the other.

It is to be understood that the phraseology or terminology employed herein is for the purpose of description and not of limitation.

All references mentioned in this application are incorporated by reference.

---

What is claimed is:

1. The microorganism *Zymomonas mobilis* containing exogenous genes encoding L-arabinose isomerase, L-ribulokinase, L-ribulose-5-phosphate-4-epimerase, transaldolase and transketolase which is capable of growing on arabinose as a sole carbon source and fermenting said arabinose to ethanol, wherein said microorganism without said genes is incapable of fermenting said arabinose to ethanol.

2. The microorganism of claim 1, wherein said transaldolase and transketolase genes, are expressed under the control of the *Z. mobilis* enolase promoter.

3. The microorganism of claim 1, wherein said
L-arabinose isomerase, L-ribulokinase, and L-ribulose 5-phosphate 4-epimerase genes are expressed under the control *Z. mobilis* glyceraldehyde-3-phosphate dehydrogenase promotor.

4. The microorganism of claim 1 wherein said exogenous genes are obtained from a microorganism selected from the group consisting of *E. coli*, Xanthomonas, Klebsiella, Rhodobacter, Flavobacterium, Acetobacter, Gluconobacter, Rhizobium, Agrobacterium, Salmonella and Pseudomonads.

5. The microorganism of claim 1 wherein said exogenous genes are expressed under the control of one or more promoters located 5' to said genes, whereby said genes are expressed in said microorganism.

6. The microorganism of claim 4, wherein the genes are integrated into the host genome.

7. The microorganism of claim 4, wherein said genes are contained on a vector.

8. The microorganism of claim 7, wherein said vector is a plasmid.

9. A vector for the transformation of *Zymomonas mobilis* comprising genes encoding L-arabinose isomerase, L-ribulokinase, L-ribulose 5-phosphate 4-epimerase, transaldolase and transketolase, and at least one promotor selected from the group consisting of *Z. mobilis* glyceraldehyde-3-phosphate dehydrogenase and *Z. mobilis* enolase recognized by *Zymomonas mobilis* which regulates the expression of the genes.

10. The microorganism of claim 1, which contains a vector comprising genes encoding L-arabinose isomerase, L-ribulokinase, L-ribulose 5-phosphate 4-epimerase, transaldolase and transketolase, and at least one promoter selected from the group consisting of *Z. mobilis* glyceraldehyde-3-phosphate dehydrogenase and *Z. mobilis* enolase recognized by *Z. mobilis* which regulates the expression of the genes.

11. The microorganism of claim 4, containing exogenous genes which encode L-arabinose isomerase, L-ribulokinase, and L-ribulose 5-phosphate 4-epimerase, expressed under the control of the *Z. mobilis* glyceraldehyde-3-phosphate dehydrogenase promoter, and exogenous genes which encode transaldolase and transketolase, expressed under the control of the *Z. mobilis* enolase promoter.

12. The microorganism of claim 1, wherein, said genes are coordinately expressed.

\* \* \* \* \*

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 42 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO (i v) ANTI-SENSE: NO (v) FRAGMENT TYPE: internal (x i) SEQUENCE DESCRIPTION: SEQ ID NO:1:

CCCTCGAGCG GCCGCGTTCG ATCAACAACC CGAATCCTAT CG    42

(2) INFORMATION FOR SEQ ID NO:2:

(i) SEQUENCE CHARACTERISTICS:
        (A) LENGTH: 57 bases
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (v) FRAGMENT TYPE: internal (x i) SEQUENCE DESCRIPTION: SEQ ID NO:2:

GGTCAAAATA GGCTTGCATG TTTATTCTCC TAACTTATTA AGTAGCTATT ATATTCC    57

(2) INFORMATION FOR SEQ ID NO:3:

(i) SEQUENCE CHARACTERISTICS:
        (A) LENGTH: 46 bases
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (v) FRAGMENT TYPE: internal (x i) SEQUENCE DESCRIPTION: SEQ ID NO:3:

GTTAGGAGAA TAAACATGCA AGCCTATTTT GACCAGCTCG ATCGCG    46

(2) INFORMATION FOR SEQ ID NO:4:

(i) SEQUENCE CHARACTERISTICS:
        (A) LENGTH: 18 bases
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (v) FRAGMENT TYPE: internal (x i) SEQUENCE DESCRIPTION: SEQ ID NO:4:

GGTTGGCGTC GACAGAAC    18

(2) INFORMATION FOR SEQ ID NO:5:

(i) SEQUENCE CHARACTERISTICS:
        (A) LENGTH: 48 bases
        (B) TYPE: nucleic acid
        (C) STRANDEDNESS: single
        (D) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( x i ) SEQUENCE DESCRIPTION: SEQ ID NO:5:

CGTCTAAAAG ATTTTAAGAA AGGTTTCGAT ATGACGGACA AATTGACC   48

( 2 ) INFORMATION FOR SEQ ID NO:6:

( i ) SEQUENCE CHARACTERISTICS:
      ( A ) LENGTH: 49 bases
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( x i ) SEQUENCE DESCRIPTION: SEQ ID NO:6:

CATTTTGACT CCAGATCTAG ATTACAGCAG ATCGCCGATC ATTTTTCC   49

( 2 ) INFORMATION FOR SEQ ID NO:7:

( i ) SEQUENCE CHARACTERISTICS:
      ( A ) LENGTH: 24 bases
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( x i ) SEQUENCE DESCRIPTION: SEQ ID NO:7:

CCAGATCTCC AGTTACTCAA TACG   24

( 2 ) INFORMATION FOR SEQ ID NO:8:

( i ) SEQUENCE CHARACTERISTICS:
      ( A ) LENGTH: 47 bases
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( x i ) SEQUENCE DESCRIPTION: SEQ ID NO:8:

GGTCAATTTG TCCGTCATAT CGAAATTTTC TTAAAATCTT TTAGACG   47

( 2 ) INFORMATION FOR SEQ ID NO:9:

( i ) SEQUENCE CHARACTERISTICS:
      ( A ) LENGTH: 29 bases (B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (v) FRAGMENT TYPE: internal (xi) SEQUENCE DESCRIPTION: SEQ ID NO:9:

GCTCTAGACG ATCTGGAGTC AAAATGTCC    29

(2) INFORMATION FOR SEQ ID NO:10:

(i) SEQUENCE CHARACTERISTICS:
    (A) LENGTH: 28 bases
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (v) FRAGMENT TYPE: internal (xi) SEQUENCE DESCRIPTION: SEQ ID NO:10:

AGATCTGCGC AAACGGACAT TATCAAGG    28

(2) INFORMATION FOR SEQ ID NO:11:

(i) SEQUENCE CHARACTERISTICS:
    (A) LENGTH: 37 bases
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (v) FRAGMENT TYPE: internal (xi) SEQUENCE DESCRIPTION: SEQ ID NO:11:

GGAATTCGCG GCCGCGTTCG ATCAACAACC CGAATCC    37

(2) INFORMATION FOR SEQ ID NO:12:

(i) SEQUENCE CHARACTERISTICS:
    (A) LENGTH: 54 bases
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (v) FRAGMENT TYPE: internal (xi) SEQUENCE DESCRIPTION: SEQ ID NO:12:

CAATTGCAAT CGCCATGTTT ATTCTCCTAA CTTATTAAGT AGCTATTATA TTCC    54

( 2 ) INFORMATION FOR SEQ ID NO:13:

( i ) SEQUENCE CHARACTERISTICS:
    ( A ) LENGTH: 42 bases
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( x i ) SEQUENCE DESCRIPTION: SEQ ID NO:13:

GTTAGGAGAA  ACATGGCGAT  TGCAATTGGC  CTCGATTTTG  GC  42

( 2 ) INFORMATION FOR SEQ ID NO:14:

( i ) SEQUENCE CHARACTERISTICS:
    ( A ) LENGTH: 21 bases
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( x i ) SEQUENCE DESCRIPTION: SEQ ID NO:14:

CGGGCGGGTG  GTACCGGAAA  G  21

( 2 ) INFORMATION FOR SEQ ID NO:15:

( i ) SEQUENCE CHARACTERISTICS:
    ( A ) LENGTH: 21 bases
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( x i ) SEQUENCE DESCRIPTION: SEQ ID NO:15:

CTTTCCGGTA  CCACCCGCCC  G  21

( 2 ) INFORMATION FOR SEQ ID NO:16:

( i ) SEQUENCE CHARACTERISTICS:
    ( A ) LENGTH: 50 bases
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( x i ) SEQUENCE DESCRIPTION: SEQ ID NO:16:

```
CTAACATGTT      GACTCCTTCT      CTAGACTTAG      CGACGAAATC      CGTAATACAC          50
```

( 2 ) INFORMATION FOR SEQ ID NO:17:

( i ) SEQUENCE CHARACTERISTICS:
        ( A ) LENGTH: 50 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( x i ) SEQUENCE DESCRIPTION: SEQ ID NO:17:

```
CGGATTTCGT      CGCTAAGTCT      AGAGAAGGAG      TCAACATGTT      AGAAGATCTC          50
```

( 2 ) INFORMATION FOR SEQ ID NO:18:

( i ) SEQUENCE CHARACTERISTICS:
        ( A ) LENGTH: 39 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( x i ) SEQUENCE DESCRIPTION: SEQ ID NO:18:

```
CCCCCAAGCT      TGCGGCCGCG      GCCCGTTGTC      CGTCGCCAG           39
```